(12) United States Patent
Koestlin et al.

(10) Patent No.: US 11,591,568 B2
(45) Date of Patent: Feb. 28, 2023

(54) GRANULOCYTIC MYELOID-DERIVED SUPPRESSOR CELLS (GR-MDSC) ACCUMULATE IN HUMAN BREASTMILK

(71) Applicant: Eberhard Karls Universitaet Tuebingen Medizinische Fakultaet, Tuebingen (DE)

(72) Inventors: Natascha Koestlin, Tuebingen (DE); Christian Gille, Tuebingen (DE)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 693 days.

(21) Appl. No.: 16/431,421

(22) Filed: Jun. 4, 2019

(65) Prior Publication Data

US 2019/0376035 A1    Dec. 12, 2019

Related U.S. Application Data

(60) Provisional application No. 62/681,373, filed on Jun. 6, 2018.

(51) Int. Cl.
  *C12N 5/0787* (2010.01)
  *A61K 35/15* (2015.01)
  *C07K 16/28* (2006.01)

(52) U.S. Cl.
  CPC ............ *C12N 5/0642* (2013.01); *A61K 35/15* (2013.01); *C07K 16/2803* (2013.01)

(58) Field of Classification Search
  None
  See application file for complete search history.

(56) References Cited

U.S. PATENT DOCUMENTS

| | | | |
|---|---|---|---|
| 2017/0189526 A1* | 7/2017 | Zhou | C07K 16/2818 |
| 2018/0078581 A1* | 3/2018 | Wang | A61P 29/00 |
| 2019/0029984 A1* | 1/2019 | Tavazoie | A61P 31/12 |

OTHER PUBLICATIONS

Köstlin et al., Front Immunol. May 17, 2018;9:1098 (Year: 2018).*
Beninson et al., "Exosomes: An emerging factor in stress-induce immunomodulation," Semin Immunol, 2014. 26(5): 394-401 http://dx.doi.org/10.1016/j.smim.2013.12.001.
Brandau et al., "Myeloid-derived suppressor cells in the peripheral blood of cancer patients contain a subset of immature neutrophils with impaired migratory properties," J Leukoc Biol, 2011. 89(2): p. 311-317 doi: 10.1189/jlb.0310162.
Costanza et al., "Prolactin: A versatile regulator of inflammation and autoimmune pathology," Autoimmun Rev, 2015. 14(3): p. 223-230 http://dx.doi.org/10.1016/j.autrev.2014.11.005.
Delano et al., "MyD88-dependent expansion of an immature GR-1+ CD11b+ population induces T cell suppression and Th2 polarization in sepsis," J Exp Med, 2007. 204(6): p. 1463-1474 www.jem.org/cgi/doi/10.1084/jem.20062602.
Dong et al., "17β-estradiol contributes to the accumulation of myeloid-derived suppressor cells in blood by promoting TNF-α secretion," Acta Biochim Biophys Sin (Shanghai), 2015. 47(8): p. 620-629 doi: 10.1093/abbs/gmv053.
Farquhar et al., "CC and CXC Chemokines in Breastmilk are Associated with Mother-to-Child HIV-1 Transmission," Curr HIV Res, 2005. 3(4): p. 361-369.
Gabitass et al., "Elevated myeloid-derived suppressor cells in pancreatic, esophageal and gastric cancer are an indpendent prognostic factor and are associated with significant elevation of the Th12 cytokine interleukin-13," Cancer Immunol Immunother (2011) 60:1419-1430 Doi 10.1007/S00262-011-1028-0.
Gabriela et al., "Oxytocin Affects Nitric Oxide and Cytokine Production by Sepsis-Sensitized Macrophages," Neuroimmunomodulation 2013;20:65-71 DOI: 10.1159/000345044.
Gabrilovich et al., "Myeloid-derived suppressor cells as regulators of the immune system," Nat Rev Immunol, 2009. 9(3): p. 162-174 doi: 10.1038/nri2506.
Gervass et al., "Myeloid Derived Suppressor Cells Are Present at High Frequency in Neonates and Suppress In Vitro T Cell Responses," PLoS One, 2014. 9(9): p. e107816 (7 pages) doi:10.1371/journal.pone.0107816.
Good et al., "Breast milk protects against the development of necrotizing enterocolitis through inhibition of Toll-like receptor 4 in the intestinal epithelium via activation of the epidermal growth factor receptor," Mucosal Immunol, 2015. 8(5): p. 1166-1179 doi:10.1038/mi.2015.30.
Greten et al., "Myeloid derived suppressor cells in human diseases," Int Immunopharmacol, 2011. 11(7): p. 802-807 doi:10.1016/j.intimp.2011.01.003.
Hassiotou et al., "Cells in Human Milk: State of the Science," J Hum Lact, 2013. 29(2): p. 171-182 doi:10.1177/0890334413477242.
Highfill et al., "Bone marrow myeloid-derived suppressor cells (MDSCs) inhibit graft-versus-host disease (GVHD) via an arginase-1-dependent mechanism that is up-regulated by interleukin-13," Blood, 2010. 116(25): p. 5738-5747 doi:10.1182/blood-2010-06-287839.
Kang et al., "Granulocytic myeloid-derived suppressor cells maintain feto-maternal tolerance by inducing Foxp3 expression in CD4+ CD25-T cells by activation of the TGF-beta/beta-catenin pathway," Mol Hum Reprod, 2016. 22(7): p. 499-511 doi:10.1093/molehr/gaw026.
Kielar et al., "Nitric Oxide Inhibits INFg-Induced Increases in CIITA mRNA Abundance and Activation of Dependent Genes—Class II MHC, Ii and H-2M," Class II TransActivator. Inflammation, 2000. 24(5): p. 431-445.
Kostlin et al., "Granulocytic myeloid derived suppressor cells expand in human pregnancy and modulate T-cell responses," Eur. J. Immunol. 2014. 44: 2582-2591 DOI: 10.1002/eji.201344200.
Kostlin et al., "HLA-G promotes myeloid-derived suppressor cell accumulation and suppressive activity during human pregnancy through engagement of the receptor ILT4," Eur. J. Immunol. 2017. 47: 374-384 DOI: 10.1002/eji.201646564.

(Continued)

*Primary Examiner* — Daniel C Gamett
(74) *Attorney, Agent, or Firm* — Rimon, P.C.

(57) ABSTRACT

The present invention relates to myeloid-derived suppressor cells (MDSC) and exosomes derived therefrom (MDSC exo) and application thereof.

13 Claims, 7 Drawing Sheets

(56) References Cited

OTHER PUBLICATIONS

Kotlin et al., "Granulocytic myeloid-derived suppressor cells from human cord blood modulate T-helper cell response towards an anti-inflammatory phenotype," Immunology, 2017 doi:10.1111/imm.12751.

Kostlin, N., et al., Granulocytic Myeloid-Derived Suppressor Cells Accumulate in Human Placenta and Polarize toward a Th2 Phenotype. J Immunol, 2016. 196(3): p. 1132-45 www.jimmunol.org/cgi/doi/10.4049/jimmunol.1500340.

Leaphart et al., "A Critical Role for TLR4 in the Pathogenesis of Necrotizing Enterocolitis by Modulating Intestinal Injury and Repair," J Immunol, 2007. 179(7): p. 4808-4820 doi: 10.4049/jimmunol.179.7.4808.

Lechner et al., "Characterization of Cytokine-Induced Myeloid-Derived Suppressor Cells from Normal Human Peripheral Blood Mononuclear Cells," J Immunol, 2010. 185(4): p. 2273-2284 https://doi.org/10.4049/jimmunol.1000901.

Lechler et al., "Functional characterization of human Cd33+ and Cd11b+ myeloid-derived suppressor cell subsets induced from peripheral blood mononuclear cells cocultured with a diverse set of human tumor cell lines," Journal of Translational Medicine 2011, 9:90 http://www.translational-medicine.com/content/9/1/90.

Lei et al., "Myeloid-Derived Suppressor Cells Impair Alveolar Macrophages through PD-1 Receptor Ligation during Pneumocystis Pneumonia," Infect Immun, 2015. 83(2): p. 572-582 doi:10.1128/IAI.02686-14.

Makarenkova et al., "CD11b+/Gr-1+ Myeloid Suppressor Cells Cause T Cell Dysfunction after Traumatic Stress," J Immunol, 2006. 176(4): p. 2085-2094 doi: 10.4049/jimmunol.176.4.2085.

Mandruzzato et al., "IL4Ra+Myeloid-Derived Suppressor Cell Expansion in Cancer Patients," J Immunol, 2009. 182(10): p. 6562-6568 www.jimmunol.org/cgi/doi/10.4049/jimmunol.0803831.

Maschmann et al., "Characterization of Human Breast Milk Leukocytes and Their Potential Role in Cytomegalovirus Transmission to Newborns," Neonatology 2015;107:213-219 DOI: 10.1159/000371753.

Ostrand-Rosenberg, S., et al., Frontline Science: Myeloid-derived suppressor cells (MDSCs) facilitate maternal-fetal tolerance in mice. J Leukoc Biol, 2017. 101(5): p. 1091-1101 DOI: 10.1189/jlb.1HI1016-306RR.

Pan et al., "17beta-estradiol enhances the expansion and activation of myeloid-derived suppressor cells via signal transducer and activator of transcription (STAT)-3 signalling in human pregnancy," 2016 British Society for Immunology, Clinical and Experimental Immunology, 185: 86-97 doi:10.1111/cei.12790.

Pan et al., "Myeloid-derived suppressor cells are essential for maintaining feto-matemal immunotolerance via STAT3 signaling in mice," Journal of Leukocyte Biology, vol. 100, Sep. 2016, p. 499-511 DOI: 10.1189/jlb.1A1015-481RR.

Noman et al., "PD-L1 is a novel direct target of HIF-1a, and its blockade under hypoxia enhanced MDSC-mediated T cell activation," J. Exp. Med. 2014 vol. 211 No. 5 781-790 www.jem.org/cgi/doi/10.1084/jem.20131916.

Pitt et al., "Dendritic cell-derived exosomes as immunotherapies in the fight against cancer," W. J Immunol, 2014; 193(3):1006-11 www.jimmunol.org/cgi/doi/10.4049/jimmunol.1400703.

Rieber, N., et al., "Neutrophilic myeloid-derived suppressor cells in cord blood modulate innate and adaptive immune responses," Clin Exp Immunol, 2013. 174(1): p. 45-52 doi:10.1111/cei.12143.

Rieber, N., et al., Flagellin induces myeloid-derived suppressor cells: implications for Pseudomonas aeruginosa infection in cystic fibrosis lung disease. J Immunol, 2013. 190(3): p. 1276-1284 doi: 10.4049/jimmunol.1202144.

Rowe (Ed.) et al.: Handbook of Pharmaceutical Excipients, 7th edition, 2012, Pharmaceutical Press, Pharmaceutical Development and Technology, 2013; 18(2): 544 DOI: 10.3109/10837450.2012.751408.

Schwarz et al., "Granulocytic myeloid-derived suppressor cells (GR-MDSC) accumulate in cord blood of preterm infants and remain elevated during the neonatal period," Clin Exp Immunol, 2017, 191: 328-337 doi:10.1111/cei.13059.

Iseri et al., "Oxytocin Protects Against Sepsis-Induced Multiple Organ Damage: Role of Neutrophils," Journal of Surgical Research 126, 73-81 (2005) doi:10.1016/j.jss.2005.01.021.

Trend et al., "Leukocyte Populations in Human Preterm and Term Breast Milk Identified by Multi-colour Flow Cytometry," PLoS One, 2015. 10(8): p. e0135580 (17 pages) DOI:10.1371/journal.pone.0135580.

Twigger, A.J., et al., "Gene expression in breastmilk cells is associated with maternal and infant characteristics," Sci Rep, 2015. 5: p. 12933 (14 pages) DOI: 10.1038/srep12933.

Watson et al., "Cytokine signalling in mammary gland development," J Reprod Immunol, 2011. 88(2): p. 124-129 doi:10.1016/j.jri.2010.11.006.

* cited by examiner

GRANULOCYTIC MYELOID-DERIVED SUPPRESSOR CELLS (GR-MDSC) ACCUMULATE IN HUMAN BREASTMILK

CROSS-REFERENCE TO RELATED APPLICATIONS

The entire contents of these priority applications are incorporated herein by reference. This application claims priority from U.S. provisional patent application Ser. No. 62/681,373, filed on 6 Jun. 2018. The entire content of this prior application is incorporated herein by reference.

FIELD OF THE INVENTION

This invention relates to myeloid-derived suppressor cells (MDSC) and exosomes derived therefrom (MDSC exo) and application thereof, which belongs to the fields of cell biology, molecular biology and clinical application. Specifically, the present invention relates to the preparation of MDSC and MDSC exo by isolation from a new biological source and their application in the treatment of diseases.

BACKGROUND OF THE INVENTION

Nosocomial bacterial infections (NBI) and necrotizing enterocolitis (NEC) are among the main reasons for death in preterm infants. Both are often caused by bacteria coming from the infected infant's gut. Despite the highly specialized interventions and policies, the rate of infection is still high due to the emergence of antimicrobial-resistant bacteria.

RELATED PRIOR ART

Myeloid derived suppressor cells (MDSC) are myeloid cells with suppressive activity on innate and adaptive immune cells primarily described in cancer patients suppressing immune response against the tumour [Gabrilovich, D. I. and S. Nagaraj, *Myeloid-derived suppressor cells as regulators of the immune system.* Nat Rev Immunol, 2009. 9(3): p. 162-74]. On basis of their surface markers, MDSC can be subdivided in granulocytic MDSC (GR-MDSC) expressing granulocytic markers like CD66b and/or CD15 and monocytic MDSC (MO-MDSC) expressing the monocytic antigen CD14 [Greten, T. F., M. P. Manns, and F. Korangy, *Myeloid derived suppressor cells in human diseases.* Int Immunopharmacol, 2011. 11(7): p. 802-7]. Differentiation of GR-MDSC from mature granulocytes in peripheral blood is—besides demonstrating their suppressive activity—mainly possible by separation according to their density [Brandau, S., et al., *Myeloid-derived suppressor cells in the peripheral blood of cancer patients contain a subset of immature neutrophils with impaired migratory properties.* J Leukoc Biol, 2011. 89(2): p. 311-7], since GR-MDSC sediment with the low density fraction. The main mechanisms by which MDSC exert their suppressive activity on other immune cells are the depletion of arginine and tryptophan by expression of effector enzymes Arginase I (ArgI), inducible NO-synthase (iNOS) and indolamin-2, 3-dioxygenase (IDO), as well as the production of reactive oxygen species (ROS) [Gabrilovich, D. I. and S. Nagaraj, loc. cit.].

Recently, it was shown that GR-MDSC, but not MO-MDSC accumulate during pregnancy in the maternal and foetal organism contributing to maternal-foetal tolerance on the one hand and to postnatal immune adaptation in neonates on the other [Kostlin, N., et al., *Granulocytic myeloid derived suppressor cells expand in human pregnancy and modulate T-cell responses.* Eur J Immunol, 2014. 44(9): p. 2582-91; Kostlin, N., et al., *Granulocytic Myeloid-Derived Suppressor Cells Accumulate in Human Placenta and Polarize toward a Th2 Phenotype.* J Immunol, 2016. 196(3): p. 1132-45; Kostlin, N., et al., *HLA-G promotes myeloid-derived suppressor cell (MDSC) accumulation and suppressive activity during human pregnancy through engagement of the receptor ILT4.* Eur J Immunol, 2016; Kostlin, N., et al., *Granulocytic myeloid derived suppressor cells from human cord blood modulate T-helper-cell response towards an anti-inflammatory phenotype.* Immunology, 2017; Rieber, N., et al., *Neutrophilic myeloid-derived suppressor cells in cord blood modulate innate and adaptive immune responses.* Clin Exp Immunol, 2013. 174(1): p. 45-52; Schwarz, J., et al., *Granulocytic myeloid-derived suppressor cells (GR-MDSC) accumulate in cord blood of preterm infants and remain elevated during the neonatal period.* Clin Exp Immunol, 2017]. Although it is well known that BM contains lots of immune cells [Hassiotou, F., D. T. Geddes, and P. E. Hartmann, *Cells in human milk: state of the science.* J Hum Lact, 2013. 29(2): p. 171-82; Trend, S., et al., *Leukocyte Populations in Human Preterm and Term Breast Milk Identified by Multicolour Flow Cytometry.* PLoS One, 2015. 10(8): p. e0135580], nothing is known about the occurrence and function of MDSC in human BM.

It has been described by the authors of US 2018/0078581 that granulocytic-like myeloid-derived suppressor cells (GR-MDSC) derived exosomes (GR-MDSC exo) may have a beneficial effect in the treatment of autoimmune diseases.

Exosomes are membranous vesicles released into extracellular environment after fusion of intracellular multivesicular complete with the plasma membrane. It has been demonstrated that almost all living cells can secrete exosomes, and exosomes widely exist in various body fluids (Beninson L A, M. Fleshner. Exosomes: an emerging factor in stress-induced immunomodulatioall. Semin Immunol, 2014. 26(5): 394-401). Exosomes carry protein, mRNA and miRNA and other ingredients derived from the derived cells, and protect them from degradation by the external environment, and are beneficial to their biological function of active ingredients. Exosomes can be internalized by receptor cells through giant pinocytosis, lipid rafts and receptor-mediated endocytosis etc. and the internalized exosomes can regulate and control multiple biological function of receptor cells and play an important role in intercellular communication. The roles of exosomes in the process of immune response, apoptosis, angiogenesis, inflammation reaction, and tumor occurrence and development have been reported. Studies showed that exosomes exhibited more advantages than derived cells when they were used in disease intervention. It had been reported that dendritic cell-derived exosomes were used to treat cancer and showed good efficacy (Pitt J M, Charrier M, Viaud S, et al. Dendritic cell-derived exosomes as immunotherapies in the fight against cancer W. J Immunol, 2014; 193(3):1006-11.).

However, so far the preparation of G-MDSC or GR-MDSC exo is a time-consuming and labour-intensive process. It requires the establishment of tumor-bearing mice or collagen-induced arthritis mice and the isolation of the GR-MDSC or GR-MDSC exo from spleen. Further, because of the origin from a tumor-bearing mouse a clinical application in humans may cause incalculable risks.

Therefore, there is still a strong need in the art for the provision of MDSC or MDSC exo, in particular G-MDSC or G-MDSC exo.

SUMMARY OF THE INVENTION

Against this background it is an object underling the invention to provide a novel method for preparing MDSC or MDSC exo, in particular G-MDSC or G-MDSC exo originating from a safe source, which enables their use in therapy while, at the same time, reducing the risk of potential side effects.

The present invention satisfies these and other needs.

The problem is solved by providing a method of preparing myeloid-derived suppressor cells (MDSC) comprising a step of isolating MDSC from breast milk.

This problem is also solved by a method of preparing myeloid-derived suppressor cells (MDSC) derived exosomes (MDSC exo) comprising a step of isolating MDSC exo from breast milk.

The inventors have realised for the very first time that MDSC and exosomes derived therefrom or extracellular vesicles derived from MDSC, respectively, can be found in and isolated from breast milk (BM). This allows the preparation of MDSC or MDSC exo by a simple isolation method and, at the same time, potentially allows their clinical applicability and use in humans.

It has been described that feeding infants with BM, suffering from certain diseases such as nosocomial bacterial infections (NBI) and necrotizing enterocolitis (NEC), might be beneficial in their pathogenesis. However, mechanisms causing the protective effect of BM are only incompletely understood. Myeloid derived suppressor cells (MDSC) are myeloid cells with suppressive activity on other immune cells, recently described to play a role in mediating maternal-fetal tolerance during pregnancy and immune adaptation in newborns. Until now, nothing has been known about occurrence of MDSC in BM.

The inventors analysed MDSC in BM and peripheral blood of breastfeeding mothers and found that granulocytic MDSC (GR-MDSC), but not monocytic MDSC (MO-MDSC), accumulate in BM, exhibit an activated phenotype and increased suppressive activity and modulate TLR-expression on monocytes. Furthermore, the inventors found that the lactotrophic hormones prolactin and oxytocin do not induce MDSC from peripheral blood. Finally, it was found that exosomes derived from MDSC or GR-MDSC, respectively, do have beneficial properties on various diseases such as gut inflammations, NBI or NEC. This is the first study to describe MDSC and exosomes derived therefore with immune-modulatory properties in human BM.

In an embodiment the method of preparing MDSC includes the following sub-steps:
providing breast milk obtained from a breastfeeding female individual,
centrifuging the breast milk to pelletize the milk cells,
discarding the supernatant and washing the pelletized milk cells to obtain the MDSC.

In another embodiment of the invention the pelletized milk cells are incubated with an anti-MDSC antibody, followed by a separation of MDSC complexed with the anti-MDSC antibody, followed by a disengagement of the MDSC from the anti-MDSC antibody, thereby obtaining the MDSC.

In yet another embodiment of the invention the anti-MDSC antibody is an anti-CD66b antibody.

In a further embodiment of the invention the MDSC comprise granulocytic myeloid-derived suppressor cells (GR-MDSC).

In an embodiment of the invention the obtained MDSC are subjected to a density gradient centrifugation to separate granulocytic myeloid-derived suppressor cells (GR-MDSC) from monocytic myeloid-derived suppressor cells (MO-MDSC).

In a further embodiment of the method of preparing MDSC exo the following steps are comprised:
providing isolated MDSC from breast milk,
cultivating said isolated MDSC in cell culture medium,
centrifuging said MDSC containing cell culture medium to obtain a supernatant and a pellet, and
isolating MDSC exo from the supernatant.

In another embodiment of the invention the isolation of MDSC exo from the supernatant includes one or more of the following procedures: centrifugation, ultracentrifugation, filtration, membrane filtration, microporous membrane filtration.

In yet another embodiment of the invention the MDSC exo comprise granulocytic myeloid-derived suppressor cells derived exosomes (GR-MDSC exo).

Another subject-matter of the invention is a method of treatment of a living being, comprising the administration of myeloid-derived suppressor cells (MDSC) and/or myeloid-derived suppressor cells (MDSC) derived exosomes (MDSC exo) isolated from breast milk. Here it is preferred if the MDSC are provided by the method of preparing MDSC according to the invention.

The features, characteristics, advantages and embodiments described for the method of preparing MDSC and MDSC exo apply likewise to this subject-matter.

In an embodiment of this method the MDSC comprise granulocytic myeloid-derived suppressor cells (GR-MDSC).

In still another embodiment of the invention the treatment is a treatment of a pathological condition selected from the group consisting of: bacterial infection, nosocomial bacterial infection (NBI), immune system disorder, inflammation, neonatal inflammation, enterocolitis, necrotizing enterocolitis (NEC), autoimmune disease.

As the inventors were able to demonstrate MDSC and MDSC exo can be used to treat or prevent above diseases, including to regulate inflammations in the gut and, therefore, to prevent an intestinal barrier disturbance.

In another embodiment the living being is selected from the group consisting of: human new-born, human very low birth weight infant (VLBW).

Another subject-matter relates to a pharmaceutical preparation comprising, as an active agent, MDSC and/or MDSC exo isolated from breast milk, and a pharmaceutically acceptable carrier.

The features, characteristics, advantages and embodiments described for the method of preparing MDSC and MDSC exo apply likewise to this subject-matter.

For this purpose, a "pharmaceutically acceptable carrier" is understood to mean any excipient, additive, or vehicle that is typically used in the field of the treatment of the mentioned diseases and which simplifies or enables the administration of the product according to the invention to a living being, and/or improves its stability and/or activity. The pharmaceutical composition can also incorporate binding agents, diluting agents or lubricants. The selection of a pharmaceutical carrier or other additives can be made on the basis of the intended administration route and standard pharmaceutical practice. As pharmaceutical acceptable carrier use can be made of solvents, extenders, or other liquid binding media such as dispersing or suspending agents, surfactant, isotonic agents, spreaders or emulsifiers, preservatives, encapsulating agents, solid binding media, depending upon what is best suited for the respective dose regime and is likewise compatible with the compound according to the invention. An overview of such additional ingredients can be found in, for example, Rowe (Ed.) et al.: Handbook of Pharmaceutical Excipients, 7th edition, 2012, Pharmaceutical Press.

In an embodiment of the invention the pharmaceutical preparation is an orally applicable pharmaceutical preparation.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention.

The invention is also described and explained in further detail by referring to the drawings.

BRIEF DESCRIPTION OF THE DRAWINGS

FIG. 4: TLR-expression on monocytes under the influence of GR-MDSC from breast milk. GR-MDSC were enriched from breast milk and added to PBMC isolated from a healthy adult control. After five days of culture, surface staining for TLR2 and TLR4 was performed and cells were analyzed by flow cytometry. (A+D) Representative histograms of TLR4- (A) and TLR2- (D) expression with (grey histograms) and without (white histograms) addition of GR-MDSC from breast milk. (B+E) Bar graphs showing the percentage of TLR4- (B) and TLR2- (E) expressing monocytes with (grey bars) and without (white bars) addition of BM-MDSCs. (C+F) Bar graphs showing the MFI of TLR4- (C) and TLR2- (F) expression on monocytes without addition of BM-MDSCs (white bars) and with addition of BM-MDSCs (grey bars). Bars represent pooled data from 6 independent experiments and each point represents an individual sample. *p<0.05, ns not significant; Wilcoxon matched pairs signed rank test.

FIG. 5: Effect of oxytocin and prolactin on induction of MDSC from PBMC. PBMC from healthy non-pregnant donors were cultured for 6 days either in medium only, in medium with 1 ng/ml GM-CSF, or in medium with oxytocin (OXY) or prolactin (PRL) in indicated concentrations. After 6 days, cells were harvested and percentages of CD33$^+$ cells analysed by flow cytometry. Bar graph shows percentages of CD33$^+$ MDSC after culture in medium alone (white bar), in medium with 1 ng/ml GM-CSF (light grey bar), or with oxytocin (OXY, medium grey bar) or prolactin (PRL, dark grey bar) in indicated concentrations. Bars represent pooled data from 5-7 experiments and each point represents an individual sample. ns not significant; Friedmann test and Dunn's multiple comparison test.

FIG. 6: Induction of MDSC by breast milk. Breast milk (BM) was collected from healthy breastfeeding mothers. BM was diluted in a 1:1 ratio with PBS and cellular components were removed by centrifugation to obtain cell-free BM supernatant (BM SN). PBMC from healthy non-pregnant donors were cultured for 6 days either in medium only, in medium with 1 ng/ml GM-CSF, or in medium with BM SN in indicated concentrations. After 6 days, cells were harvested and percentages of CD33+ cells analysed by flow cytometry. (A+B) Bar graphs show percentages of CD33+ MDSC after culture in medium alone (white bar), in medium with 1 ng/ml GM-CSF (light grey bar), or with 25% BM SN (BM SN 25%) (A) or after culture in medium with BM SN in indicated concentrations (B). Bars represent pooled data from 7-14 experiments and each point represents an individual sample. ns not significant; Friedmann test and Dunn's multiple comparison test.

FIG. 7: Suppressive activity of breast milk supernatant induced MDSC. PBMC from a healthy donor were cultured for 6 days in medium with 25% breast milk (BM) supernatant (SN). After 6 days, cells were harvested and CD33+ cells were enriched by MACS and added to PBMC from the same donor stimulated with IL-2 and OKT3. Proliferation index was determined as ratio between T-cell proliferation with addition of MDSC and T-cell proliferation without addition of MDSC. The proliferation of T-cells alone was set on 100%. (A+B) Bar graphs show the inhibitory effect of BM SN induced MDSC on proliferation of CD4+ (A) and CD8+ T-cells (B) in different ratios. Dashed line shows proliferation of target MNC without addition of MDSC. Bars show mean and standard deviation. *$p<0.05$; Wilcoxon matched-pairs signed-rank test.

EXAMPLES

1. Introduction

The inventors analysed expression of MDSC in BM in comparison to peripheral blood of breastfeeding mothers and show that (1) GR-MDSC accumulate in BM, (2) GR-MDSC from BM (BM-MDSC), MDSC supernatant and exosomes derived from GR-MDSC (GR-MDSC exo) strongly suppress T-cell proliferation (3) BM-MDSC exhibit an activated phenotype in comparison to GR-MDSC from peripheral blood with altered expression of chemokine receptors, co-inhibitory molecules and effector enzymes and higher suppressive capacity, (4) BM-MDSC and GR-MDSC exo modulate TLR-expression of monocytes and (5) MDSC are not induced by lactotrophic hormones oxytocin and prolactin. These results point towards a novel role of GR-MDSC and GR-MDSC exo in BM for regulation of intestinal immune responses in neonates. Targeting BM-MDSC and MDSC exo might be a strategy to prevent severe complications like NBI and NEC in preterm infants.

2. Methods

Patients

The local ethics committee approved this study (682/2016BO1) and all women gave their written informed consent. From November 2016 to November 2017, breast milk and peripheral blood from breastfeeding mothers of healthy term infants were collected during routine blood sampling six weeks postpartum. Breast milk from breastfeeding mothers of preterm infants was collected during their stay in the Department of Neonatology at Tuebingen University Hospital starting in the first week of life and then weekly for six weeks. Women with chronic or acute infections at the time of sample collection were excluded from the study.

Cell Isolation and Flow Cytometry

All samples were processed within six hours after collection. Peripheral blood mononuclear cells (PBMC) were prepared from EDTA blood samples for phenotype analyses and from heparinized blood samples (4 IE/ml) for functional analyses by Ficoll density gradient centrifugation (lymphocyte separation medium, Biochrom, Berlin, Germany).

For isolation of milk cells, breast milk was diluted in a 1:1 ratio with phosphate buffered saline (PBS) and centrifuged for 20 minutes at 805 g. Supernatant was removed and cells were washed two times with PBS [Twigger, A. J., et al., *Gene expression in breastmilk cells is associated with maternal and infant characteristics.* Sci Rep, 2015. 5: p. 12933].

For GR-MDSC isolation from PBMC or milk cells, cells were labelled with anti-CD66b-FITC, followed by two sequential anti-FITC magnetic bead separation steps (MiltenyiBiotec, Bergisch-Gladbach, Germany) according to the manufacturer's instructions. Purity of CD66b+ cells after separation was >90%, as assessed by flow cytometry.

After Ficoll density gradient centrifugation GR-MDSC were characterized as $CD66b^+/CD33^+/CD14^-/HLA\text{-}DR^{low/-}$ cells and MO-MDSC as $CD14^+/HLA\text{-}DR^{low/-}$, according to previously established human MDSC characterization methods [Kostlin, N., et al., *Granulocytic Myeloid-Derived Suppressor Cells Accumulate in Human Placenta and Polarize toward a Th2 Phenotype.* J Immunol, 2016. 196(3): p. 1132-45]. Antibody against ILT4 was purchased from R&D Systems, Wiesbaden-Nordenstadt, Germany. All other antibodies for extracellular staining were purchased from BD Pharmingen, Heidelberg, Germany.

Intracellular staining for MDSC effector enzymes ArgI, iNOS and IDO was performed as described previously [Kostlin, N., et al., *Granulocytic myeloid derived suppressor cells expand in human pregnancy and modulate T-cell responses.* Eur J Immunol, 2014. 44(9): p. 2582-91]. Antibody against ArgI and IDO were purchased from R&D systems, Wiesbaden-Nordenstadt, Germany, antibody against iNOS from Santa Cruz, Heidelberg, Germany.

Data acquisition was performed with a FACScalibur flow cytometer (BD Bioscience) and analysed via CellQuest (BD Biosciences).

Cytospins

Isolated BM-MDSCs were fixed with cytospin centrifugation and stained with May-Gruenwald-Giemsa. Images were acquired on a Carl Zeiss Fotomicroscope (×40 Planapo oil objective, Carl Zeiss, Oberkochen, Germany) using a Canon EOS 500 camera (Canon, Krefeld, Germany) and Adobe Photoshop CS3 software (Adobe Systems, Dublin, Ireland).

T-Cell Suppression Assays

PBMC from healthy, non-pregnant adults were isolated, stained with carboxyfluorescein-succinimidyl ester (CFSE, Invitrogen, Heidelberg, Germany) according to the manufacturer's instructions and stimulated with 100 U/ml Interleukin-2 (IL-2, R&D Systems, Wiesbaden-Nordenstadt, Germany) and 1 µg/ml OKT3 (Janssen-Cilag, Neuss, Germany). 60,000 PBMC per well in RPMI1640 supplemented with 10% autologous serum were seeded in a 96-well microtiter plate (BD Biosciences) and 20,000, 30,000 or 60,000 GR-MDSC in RPMI1640, isolated from PBMC of breastfeeding women or from milk cells were added. As control, only RPMI1640 was added to the PBMC. After 96 h incubation, cells were harvested and stained with anti-CD8-PE and anti-CD4-APC (BD Pharmingen). CFSE fluorescence intensity was analyzed by flow cytometry to determine proliferation of CD4+ and CD8+ T-cells. Proliferation index, defined as the ratio of T-cell proliferation after addition of GR-MDSC and T-cell proliferation without GR-MDSC, was determined. T-cell proliferation without GR-MDSC was set to a fixed value of 1.

ROS Detection

For detection of ROS, $4\times10^5$ PBMC or milk cells were incubated with dihydrorhodamine 123 (DHR, Sigma, Munich, Germany) in RPMI1640 for five minutes at 37° C. Thereafter, cells were stimulated for ten minutes with 60 ng/ml Phorbol-12 myristate-13 acetate (PMA, Sigma, Munich, Germany). Cells were washed, surface stained with anti-CD66b-APC (Ebiosciences, San Diego, Calif., USA) and ROS production was analysed by flow cytometry.

Co-Culture Experiments

PBMC from healthy, non-pregnant individuals were isolated and seeded at a concentration of 1×10$^6$ cells/ml in RPMI1640 with 10% FCS in a 24-well plate and 2.5×10$^5$ BM-MDSC were added. As control, only RPMI1640 was added to the PBMC. After five days of culture surface staining for CD66b, CD14, TLR2 and TLR4 (all from BD biosciences) was performed.

MDSC Induction

Human PBMC were isolated from heparinised blood samples (4 IE/ml) from healthy volunteer donors by Ficoll density gradient centrifugation and cultured in complete medium (Dulbecco's modified eagle medium, DMEM (Thermo Fisher Scientific, Darmstadt, Germany), supplemented with 10% foetal calf serum (FCS, Biochrom, Berlin, Germany) and 1% Penicilline/Streptomycin (Biochrom, Berlin, Germany) (5×10$^5$ cells/ml) in 12-well-plates (Greiner Bio-One GmbH, Frickenhausen, Germany) supplemented with different concentrations of prolactin (Merck KGaA, Darmstadt, Germany) and oxytocin (Hexal AG, Holzkirchen, Germany). PBMC cultured in medium alone were run in parallel as induction negative control and PBMC cultured in medium with 1 ng/ml GM-CSF (R&D systems) as induction positive control [Lechner, M. G., D. J. Liebertz, and A. L. Epstein, *Characterization of cytokine-induced myeloid-derived suppressor cells from normal human peripheral blood mononuclear cells.* J Immunol, 2010. 185(4): p. 2273-84]. After 6 days, PBMC were removed using the non-protease cell detachment solution Detachin (GenLantis, San Diego, USA). Since CD66b is down-regulated after several days of culture, we quantified and enriched MDSC using the myeloid marker CD33$^+$ according to previously described protocols [Lechler et al. 2010, loc. cit., Lechner, M. G., et al., *Functional characterization of human Cd33+ and Cd11b+ myeloid-derived suppressor cell subsets induced from peripheral blood mononuclear cells co-cultured with a diverse set of human tumor cell lines.* J Transl Med, 2011. 9: p. 90.]. CD33$^+$ cells were quantified by flow cytometry.

Statistical Analysis

Statistical analysis was done using GraphPad Prism 5.0 (GraphPad Software, La Jolla, Calif.). Data were analysed for Gaussian distribution using D'Agostino and Pearson omnibus normality test. Normally distributed data were analysed using the paired t-test, not normally distributed data were evaluated using the Wilcoxon matched pairs signed rank test. A p-value<0.05 was considered as statistically significant.

3. Results

GR-MDSC Accumulate in Human Breast Milk

Figure 1:
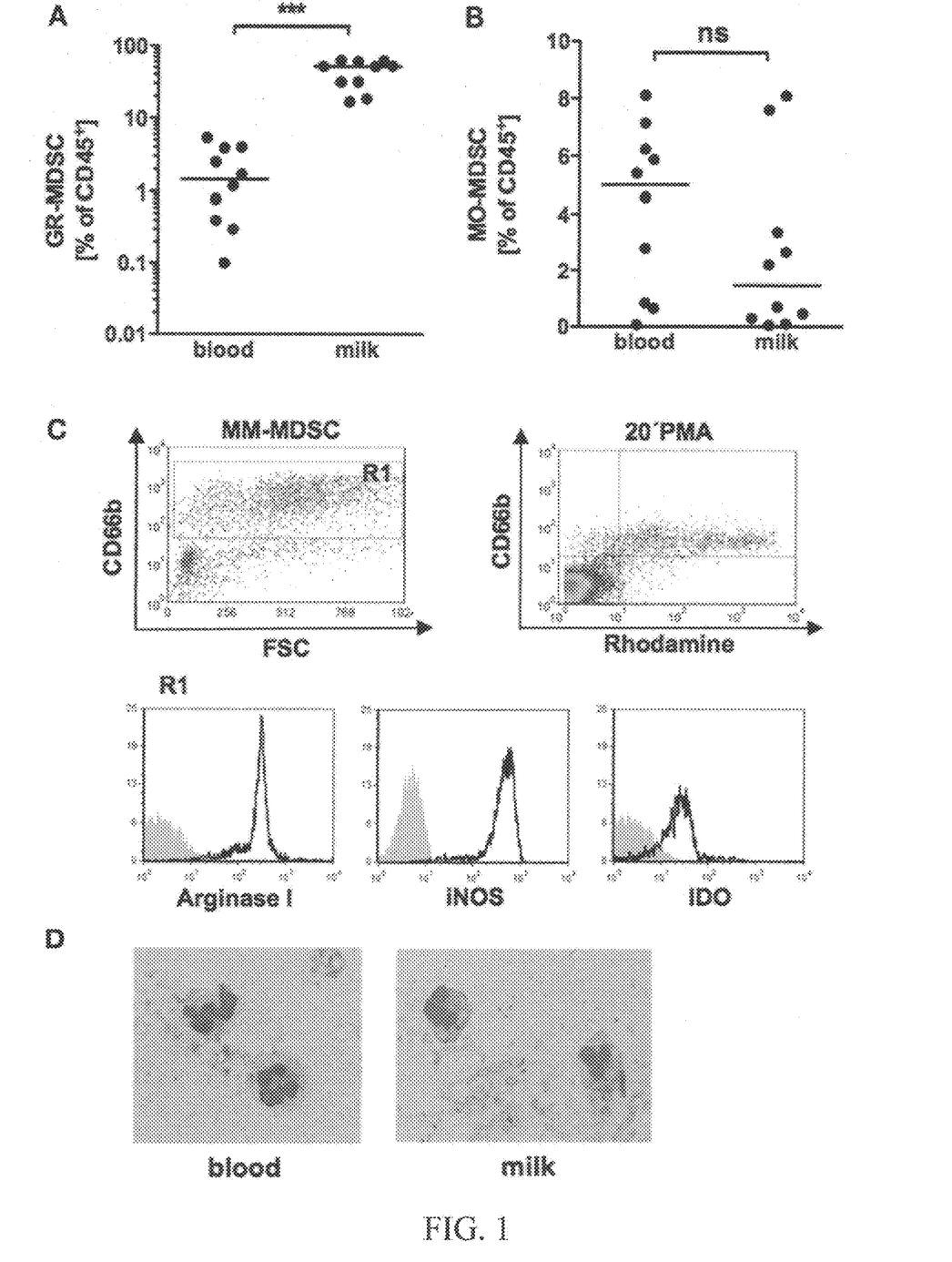
FIG. 1: Quantification of GR-MDSC and MO-MDSC in peripheral blood and breast milk of breastfeeding women. Mononuclear cells were isolated from peripheral blood of breastfeeding women and milk cells isolated from corresponding breast milk samples and analysed by flow cytometry. (A+B) Scatter diagrams showing percentages of GR-MDSC (A) and MO-MDSC (B) from peripheral blood (blood) and breast milk (milk). Plots represent 10 independent experiments. Each symbol represents an individual sample and the median is indicated. ***p<0.005; Wilcoxon matched pairs signed rank test. (B) Density plot of forward scatter versus CD66b and Rhodamine versus CD66b from CD45$^+$ milk leukocytes. Gate 1 shows the GR-MDSC population. Representative histograms show the expression of intracellular effector enzymes ArgI, iNOS and IDO on GR-MDSC from breast milk. (D) Representative cytospin of GR-MDSC enriched from milk cells by MACS.

First, the inventors analysed expression of GR-MDSC in BM of term infants in comparison to peripheral blood of the corresponding mother. They quantified MDSC in total milk cells without previous isolation of mononuclear cells, as density gradient centrifugation of single samples showed that all milk cells sedimented with the low density fraction of mononuclear cells. They found that percentages of GR-MDSC were about 20fold higher in BM than in peripheral blood (median 52.2% vs. 1.5%, p=0.001, n=10, FIG. 1A), while percentages of MO-MDSC tended to be lower in BM (median 1.4% vs. 5.0%, p=0.05, n=10, FIG. 1B). The surface phenotype of BM-MDSC and GR-MDSC from peripheral blood was characterized (not shown). As shown in FIG. 1C, BM-MDSC expressed the known effector enzymes ArgI, iNOS and IDO and produced significant amounts of ROS. BM-MDSC showed the typical morphology of granulocytic cells with segmented nucleus. Repeated measurements of BM from 4 preterm infants demonstrated that GR-MDSC counts did not decrease during the first seven postnatal weeks (not shown).

BM-MDSC Efficiently Suppress T-Cell Proliferation

Figure 2:
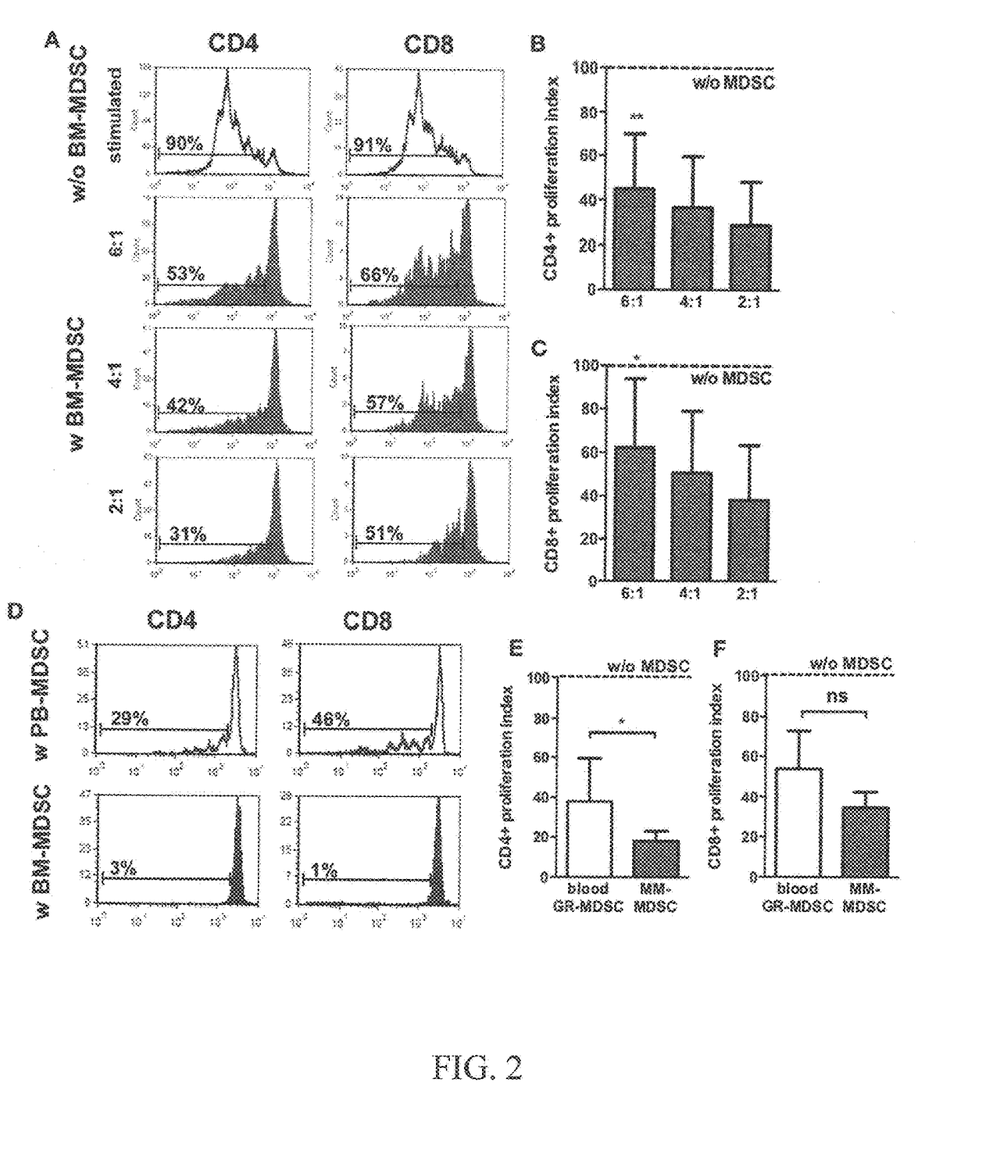
FIG. 2: Inhibition of CD4$^+$ and CD8$^+$ T-cell proliferation by GR-MDSC from breast milk. GR-MDSC were enriched from breast milk (BM-MDSC) and added to CFSE-stained and IL-2/OKT3-stimulated PBMC isolated from a healthy adult control. After four days, proliferation of CD4$^+$ and CD8$^+$ T-cells was assessed by CFSE dye dilution. Proliferation index was determined as ratio of T-cell proliferation with and without addition of BM-MDSC. (A) Representative histogram plots showing proliferation of CD4$^+$ T-cells and CD8$^+$ T-cells with (grey histograms) and without (white histograms) addition of BM-MDSC in different proportions. (B, C) Inhibitory effect of BM-MDSC on proliferation of CD4$^+$ (B) and CD8$^+$ T-cells (C). Dashed line shows proliferation of target PBMC without addition of BM-MDSC. Inhibition of T-cell proliferation by BM-MDSC was measured at the indicated ratios by CFSE dye dilution. Bars show mean and standard deviation of 7 samples pooled from 7 independent experiments. *p<0.05 compared with target cells alone; Wilcoxon matched-pairs signed-rank test. (D) Representative histogram plots (from 5 independent experiments) showing proliferation of CD4$^+$ T-cells and CD8$^+$ T-cells after stimulation with OKT3 and IL-2 and addition of GR-MDSC isolated from PBMC from peripheral blood (white histograms) and BM-MDSC of the same person (grey histograms). (E, F) The inhibitory effect of GR-MDSC from peripheral blood (blood GR-MDSC, white bars) and from BM (BM-MDSC, grey bars) on proliferation of CD4$^+$ (E) and CD8$^+$ T-cells (F) were assessed. Dashed line shows proliferation of target PBMC without addition of GR-MDSC. Inhibition of T-cell proliferation by GR-MDSC was measured at the indicated ratios by CFSE dye dilution. Bars show mean and standard deviation of 5 independent experiments. *p<0.05; ns not significant; Wilcoxon matched-pairs signed-rank test
Figure 3:
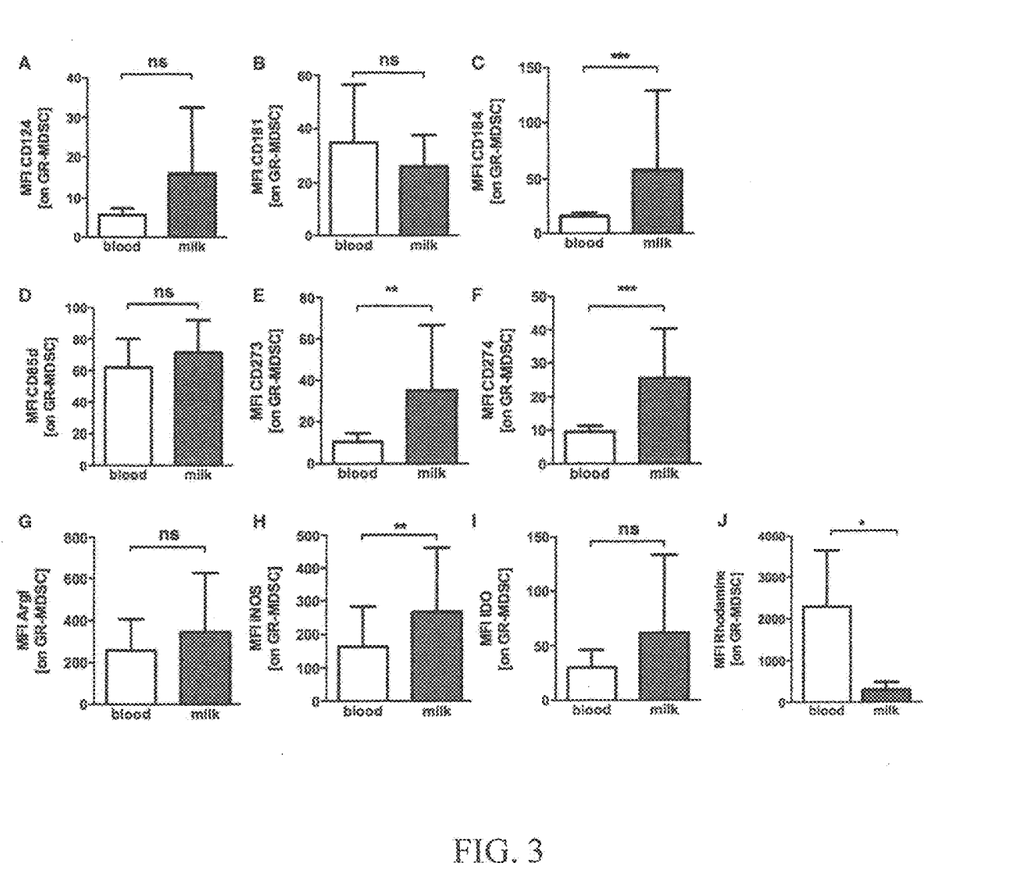
FIG. 3: Expression of chemokine receptors, co-inhibitory molecules and effector enzymes on GR-MDSC from breast milk. Mononuclear cells were isolated from peripheral blood of breastfeeding women and milk cells isolated from breast milk of the same person and analysed by flow cytometry. Intracellular staining for ArgI, iNOS and IDO was performed and ROS-production detected by DHR. Bar graphs show the MFI for receptor and enzyme expression on GR-MDSC in peripheral blood (blood, white bars) and breast milk (milk, grey bars). Bars represent data from 5-10 independent experiments and mean and standard deviation are indicated. *p<0.05; p<0.01; *p<0.005; ns, not significant; Wilcoxon matched-pairs signed rank test or paired t-test.

Next, the inventors aimed to confirm that the granulocytic cells they found in BM and hypothesized to be MDSC indeed possess suppressive activity, the main characteristic to distinguish them from mature granulocytes. Therefore, they performed T-cell-proliferation assays with enriched BM-MDSC and PBMC from healthy adult donors. FIG. 3A shows representative histogram plots for proliferation of adult and neonatal CD4$^+$ and CD8$^+$ T-cells with and without addition of BM-MDSC. Addition of BM-MDSC to PBMC reduced proliferation index of CD4$^+$ T-cells concentration-dependent to 45.0% (1:6), 36.6% (1:4) and 28.7% (1:2) (p<0.05, n=7, FIG. 3B). Accordingly, CD8$^+$ T-cell-proliferation was reduced concentration-dependent to 62.2% (1:6), 50.8% (1:4) and 38.0% (1:2) (p<0.05, n=7, FIG. 3C). Similar results were obtained when CBMC were used as target cells (not shown). Comparison of suppressive capacity of BM-MDSC and MDSC from peripheral blood revealed a stronger activity of BM-MDSC (proliferation index 17% vs. 38% for inhibition of CD4$^+$ T-cell proliferation and 33% vs. 58% for inhibition of CD8$^+$ T-cell proliferation, n=5, p<0.05 for CD4, not significant for CD8) (FIG. 2D-F).

Figure 4:
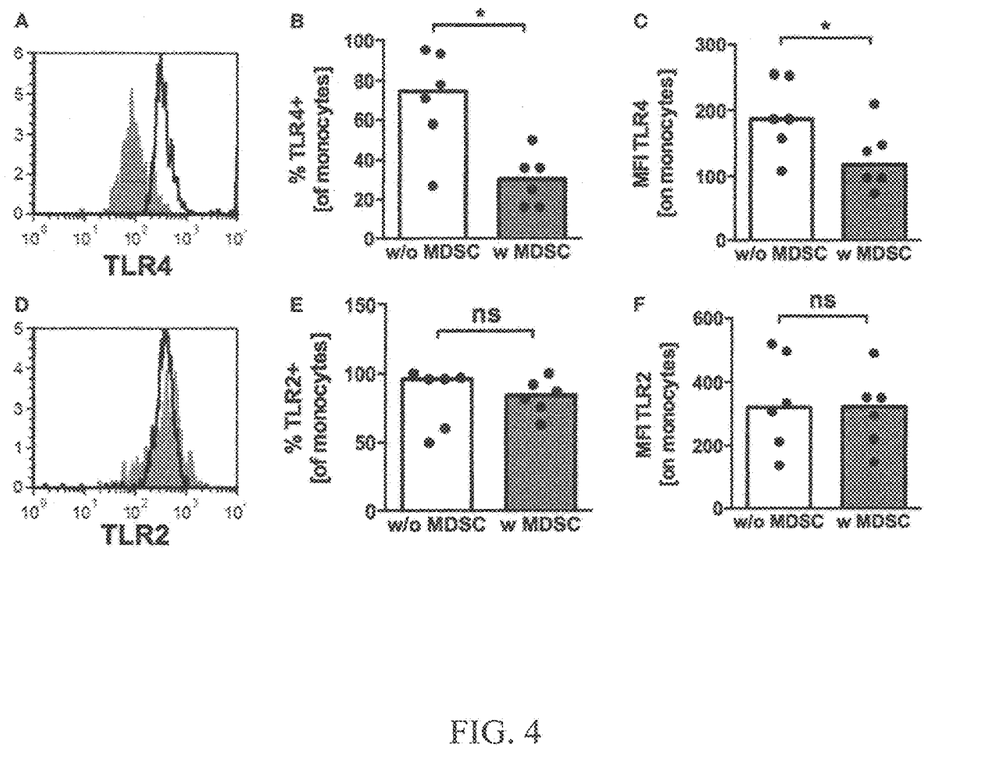

BM-MDSC Expresses Increased Levels of Chemokine Receptors, Co-Inhibitory Molecules and Effector Enzymes To get further insights into the activation state of BM-MDSC the inventors next asked whether BM-MDSC express different levels of chemokine receptors, activation markers, co-inhibitory molecules and effector enzymes than GR-MDSC from peripheral blood. BM-MDSC expressed significantly higher levels of CXCR4 (CD184) than PB-MDSC (MFI median 34.0 vs. 16.3, p=0.001, n=10 FIG. 4C), while expression of CXCR1 (CD181) and IL4Rα (CD124) was not different (FIGS. 3A+B). Expression of the inhibitory receptor ILT4 (CD85d), that was recently shown to be relevant for activation of GR-MDSC during pregnancy, also did not differ between BM-MDSC and PB-MDSC (FIG. 3D). However, BM-MDSC expressed higher levels of co-inhibitory molecules PD-L1 (CD274) and PD-L2 (CD273) than PB-MDSC (MFI median 20.0 vs. 9.0 for PD-L1 and 26.5 vs. 10.0 for PD-L2, p=0.001 and p=0.002, n=10, FIGS. 3E+F). Regarding effector mechanisms, the inventors found an increased expression of iNOS (MFI median 192.9 vs. 134.0, p=0.006, n=9, FIG. 3H) and a decreased production of ROS (MFI median 343.0 vs. 2873.0, p=0.03, n=5, FIG. 3J) by BM-MDSC, while expression of ArgI and IDO was similar in BM-MDSC and PB-MDSC (FIGS. 3G+I).

BM-MDSC Modulate TLR-Expression on Monocytes

Expression of toll like receptors on monocytes plays an important role in bacterial host defence and pathogenesis of NEC [Good, M., et al., *Breast milk protects against the development of necrotizing enterocolitis through inhibition of Toll-like receptor 4 in the intestinal epithelium via activation of the epidermal growth factor receptor.* Mucosal Immunol, 2015. 8(5): p. 1166-79; Leaphart, C. L., et al., *A critical role for TLR4 in the pathogenesis of necrotizing enterocolitis by modulating intestinal injury and repair.* J Immunol, 2007. 179(7): p. 4808-20]. Therefore, the inventors examined TLR2 and TLR4-expression on monocytes after co-culture with BM-MDSC. Both, percentages of TLR4-expressing cells (median 30.5% vs. 74.5%, p=0.02, n=6) (FIG. 4B) and TLR4-MFI (127.2±49.3 vs. 191.3±56.5, p<0.05, n=6) (FIG. 4C) were reduced on monocytes after co-culture with BM-MDSC, while expression of TLR2 remained unchanged (FIG. 4D-E).

Prolactin and Oxytocin do not Induce MDSC from PBMC

Figure 5:
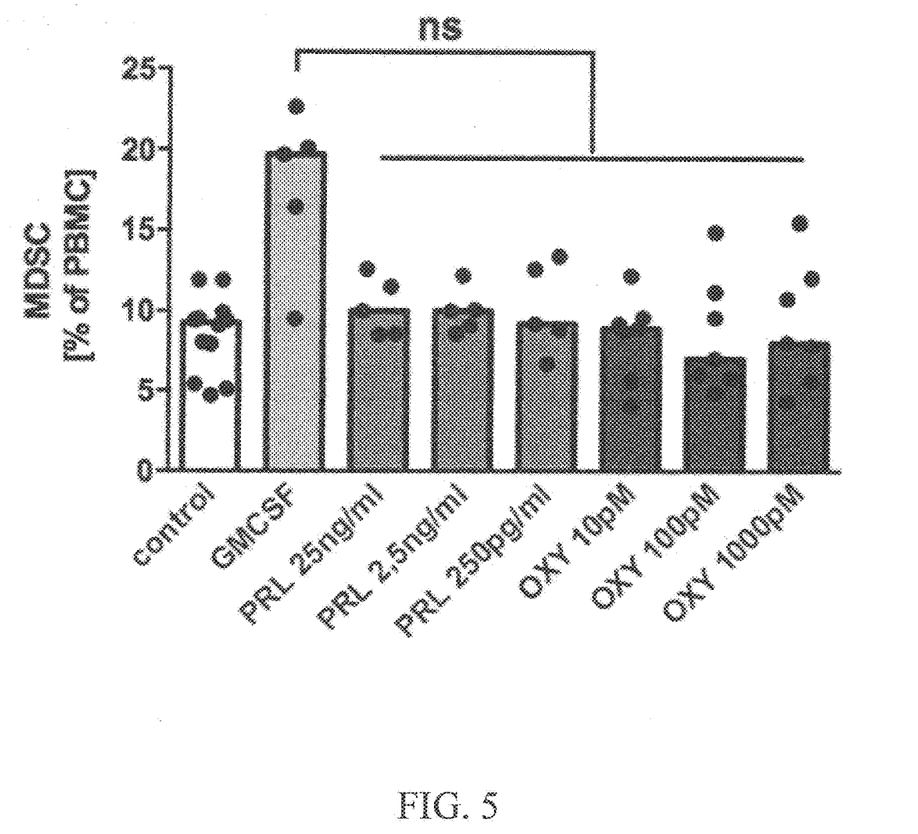

With intent to identify mechanisms by which MDSC-accumulation in BM occurs, the inventors tested the hypothesis that the lactation-associated hormones oxytocin and/or prolactin could induce MDSC from PBMC according to previously described protocols [Lechner, M. G., D. J. Liebertz, and A. L. Epstein, *Characterization of cytokine-induced myeloid-derived suppressor cells from normal human peripheral blood mononuclear cells.* J Immunol, 2010. 185(4): p. 2273-84; Kostlin, N., et al., *HLA-G promotes myeloid-derived suppressor cell accumulation and suppressive activity during human pregnancy through engagement of the receptor ILT4.* Eur J Immunol, 2017. 47(2): p. 374-384]. However, neither prolactin nor oxytocin in different concentrations could induce MDSC from PBMC (FIG. 5).

Breast Milk Supernatant Induces MDSC

Figure 6:
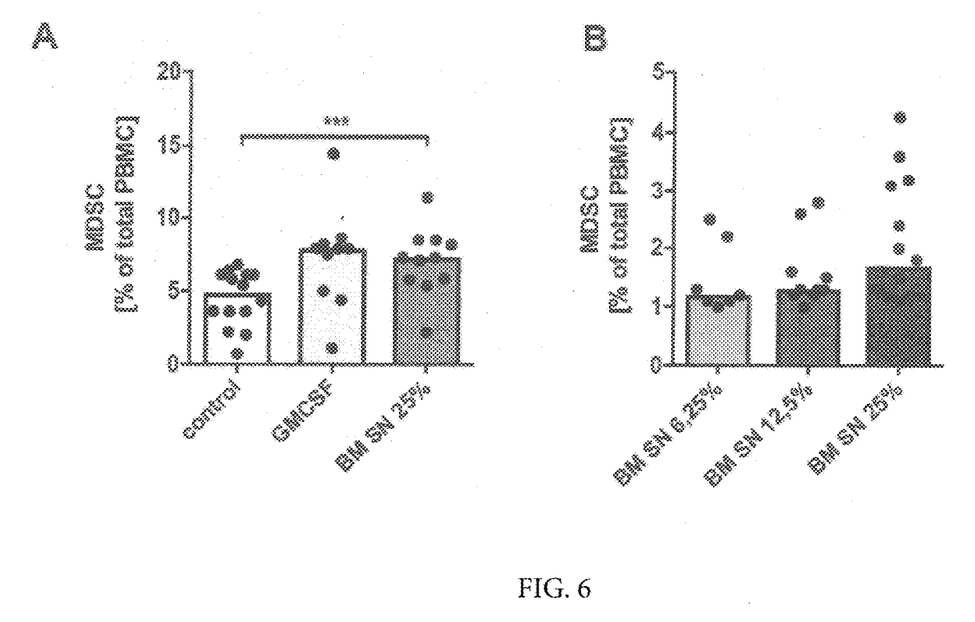

In a next experiment the inventors used supernatant of breast milk (BM) and found that the supernatant (SN) induces MDSC (FIG. 6). As BM contained high numbers of MDSC the inventors aimed to figure out if BM contains soluble factors with the potency to induce MDSC. To adress this question, the inventors cultured PBMC from healthy adults with different concentrations of cell-free supernatant from BM (BM SN) and found that PBMC cultured with BM SN contained significantly higher numbers of MDSC after culture with BM SN compared to culture in medium alone (7.1+−2.3% vs. 4.5+−1.9%, n=10-14, p<0.001, Wilcoxon matched pairs signed rank test). Addition of GM-CSF, which has been previously shown to induce MDSC from PBMC shows similar effects on MDSC-induction as BM SN did (7.3+−3.5%) (FIG. 6A). Induction of MDSC by BM SN was concentration dependent (FIG. 6B).

Inhibition of the CD4 T Cell Proliferation by MDSC Supernatant

Figure 7:
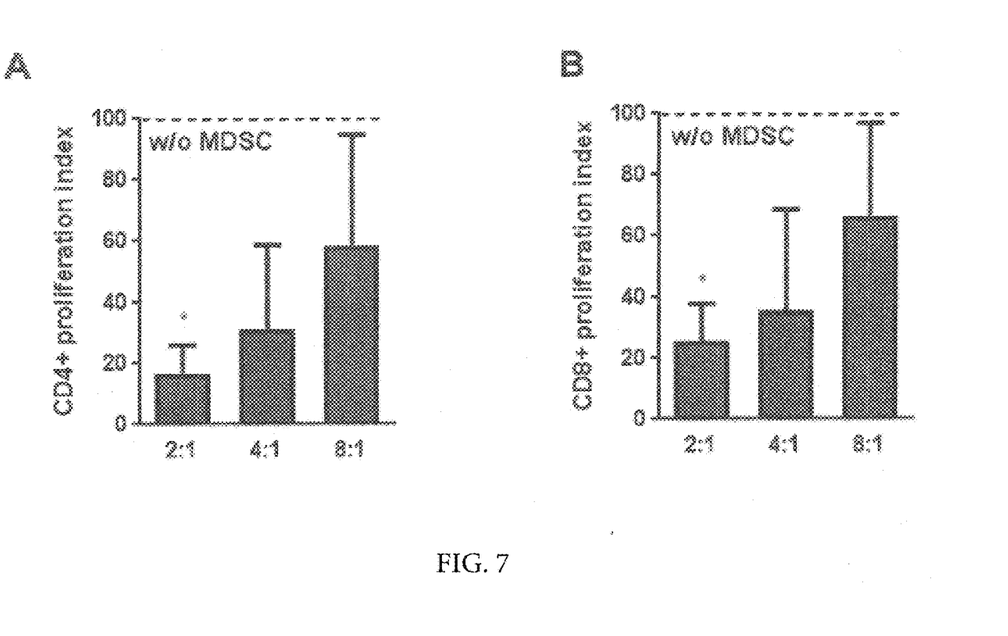

MDSC were cultured for 4 days and the supernatant was collected (snMDSC). This was added in different ratios to freshly isolated, CFSE-labeled and OKT3 and IL-2 stimulated T cells. After another 4 days, the CD4 T-cell proliferation by CFSE dilution was measured by flow cytometry. The proliferation index was determined as the quotient of CD4 cell proliferation with the addition of snMDSC and without the addition of snMDSC. The dashed line shows the CD4 T cell proliferation without snMDSC. It could be shown that the addition of MDSC induced by BM SN to OKT3- and IL-2 stimulated PBMC significantly inhibited CD4 and CD8 T-cell proliferation to 16.8% and 25.5% compared PBMC cultured alone (FIGS. 7A+B).

Isolation of MDSC Derived Exosomes and Their Activity

In another experiment the inventors isolated exosomes from MDSC (MDSC exo) by methods well know in the art, e.g. as described in US 2018/0078581. The isolation was verified by electron microscopy (data not shown). It could be demonstrated by the inventors that the isolated MDSC exo exhibit activity that is comparable with the activity as observed by the inventors for MDSC or the supernatant of cultivated MDSC (data not shown).

4. Discussion

Expression of MDSC under pathological conditions has been widely described [Brandau, S., et al., *Myeloid-derived suppressor cells in the peripheral blood of cancer patients contain a subset of immature neutrophils with impaired migratory properties.* J Leukoc Biol, 2011. 89(2): p. 311-7; Delano, M. J., et al., *MyD88-dependent expansion of an immature GR-1(+)CD11b(+) population induces T cell suppression and Th2 polarization in sepsis.* J Exp Med, 2007. 204(6): p. 1463-74; Highfill, S. L., et al., *Bone marrow myeloid-derived suppressor cells (MDSCs) inhibit graft-versus-host disease (GVHD) via an arginase*-1-*dependent mechanism that is up-regulated by interleukin*-13. Blood, 2010. 116(25): p. 5738-47; Makarenkova, V. P., et al., *CD11b+/Gr-1+ myeloid suppressor cells cause T cell dysfunction after traumatic stress.* J Immunol, 2006. 176(4): p. 2085-94; Rieber, N., et al., *Flagellin induces myeloid-derived suppressor cells: implications for Pseudomonas aeruginosa infection in cystic fibrosis lung disease.* J Immunol, 2013. 190(3): p. 1276-84.]. Beyond that, an accumulation of MDSC during healthy pregnancy both in maternal and foetal organism has been reported [Kostlin, N., et al., *Granulocytic myeloid derived suppressor cells expand in human pregnancy and modulate T-cell responses.* Eur J Immunol, 2014. 44(9): p. 2582-91; Kostlin, N., et al., *Granulocytic Myeloid-Derived Suppressor Cells Accumulate in Human Placenta and Polarize toward a Th2 Phenotype.* J Immunol, 2016. 196(3): p. 1132-45; Kostlin, N., et al., *HLA-G promotes myeloid-derived suppressor cell (MDSC) accumulation and suppressive activity during human pregnancy through engagement of the receptor ILT4.* Eur J Immunol, 2016; Kostlin, N., et al., *Granulocytic myeloid derived suppressor cells from human cord blood modulate T-helper-cell response towards an anti-inflammatory phenotype.* Immunology, 2017; Rieber, N., et al., *Neutrophilic myeloid-derived suppressor cells in cord blood modulate innate and adaptive immune responses.* Clin Exp Immunol, 2013. 174(1): p. 45-52; Schwarz, J., et al., *Granulocytic myeloid-derived suppressor cells (GR-MDSC) accumulate in cord blood of preterm infants and remain elevated during the neonatal period.* Clin Exp Immunol, 2017; Gervassi, A., et al., *Myeloid derived suppressor cells are present at high frequency in neonates and suppress in vitro T cell responses.* PLoS One, 2014. 9(9): p. e107816; Kang, X., et al., *Granulocytic myeloid-derived suppressor cells maintain feto-maternal tolerance by inducing Foxp3 expression in CD4+CD25− T cells by activation of the TGF-beta/beta-catenin pathway.* Mol Hum Reprod, 2016. 22(7): p. 499-511; Ostrand-Rosenberg, S., et al., *Frontline Science: Myeloid-derived suppressor cells (MDSCs) facilitate maternal-fetal tolerance in mice.* J Leukoc Biol, 2017. 101(5): p. 1091-1101] and a role for maternal-foetal tolerance and postnatal immune adaptation in neonates been postulated. Although it is well known that breastfeeding strongly contributes to establishment of neonatal immune defence, nothing was known on the presence and function of MDSC in breast milk. In the present study, the inventors analysed occurrence of MDSC in human breast milk and found that (1) GR-MDSC, but not MO-MDSC, accumulate in BM, (2) BM-MDSC efficiently suppress T-cell proliferation and are activated in comparison to MDSC from peripheral blood, (3) BM-MDSC exhibit an altered phenotype in comparison to peripheral blood MDSC of pregnant women, (4) BM-MDSC reduce TLR4-expression on monocytes and (5) MDSC are not induced by lactotrophic hormones prolactin and oxytocin.

The finding that GR-MDSC, but not MO-MDSC, accumulate in human breast milk is in line with results in peripheral blood of pregnant women and in cord blood of healthy newborns [Kostlin, N., et al., *Granulocytic myeloid derived suppressor cells expand in human pregnancy and modulate T-cell responses.* Eur J Immunol, 2014. 44(9): p. 2582-91; Rieber, N., et al., *Neutrophilic myeloid-derived suppressor cells in cord blood modulate innate and adaptive immune responses.* Clin Exp Immunol, 2013. 174(1): p.

45-52.], where the inventors found increased levels of GR-MDSC, while numbers of MO-MDSC were unchanged when compared with peripheral blood of healthy adults. Recent in-vitro and in-vivo data revealed that systemic accumulation of GR-MDSC during pregnancy contributes to maternal-foetal tolerance and maintenance of pregnancy [Kang, X., et al., *Granulocytic myeloid-derived suppressor cells maintain feto-maternal tolerance by inducing Foxp3 expression in CD4+CD25−T cells by activation of the TGF-beta/beta-catenin pathway.* Mol Hum Reprod, 2016. 22(7): p. 499-511; Kang, X., et al., *Granulocytic myeloid-derived suppressor cells maintain feto-maternal tolerance by inducing Foxp3 expression in CD4+CD25−T cells by activation of the TGF-beta/beta-catenin pathway.* Mol Hum Reprod, 2016. 22(7): p. 499-511], while they modulate adaptive immunity postnatally, potentially increasing the neonate's susceptibility to infections [Kostlin, N., et al., *Granulocytic myeloid derived suppressor cells from human cord blood modulate T-helper-cell response towards an anti-inflammatory phenotype.* Immunology, 2017; Schwarz, J., et al., *Granulocytic myeloid-derived suppressor cells (GR-MDSC) accumulate in cord blood of preterm infants and remain elevated during the neonatal period.* Clin Exp Immunol, 2017.]. The present study is the first describing the presence of MDSC also in breast milk. Contrary to our findings in peripheral blood of preterm infants [Schwarz et al., loc. cit.], numbers of GR-MDSC in breast milk did not decrease during the first six postnatal weeks. Transfer of BM-MDSC from mother to child beyond the neonatal period could be a mechanism for local immune modulation in the gut, where the main contact with microbes takes place.

One important factor of the inventor's study is that, due to high cell loss, quantification of MDSC in BM was performed without prior density gradient centrifugation. Since GR-MDSC and mature granulocytes exhibit the same surface phenotype and only differ by their density [Brandau, S., et al., *Myeloid-derived suppressor cells in the peripheral blood of cancer patients contain a subset of immature neutrophils with impaired migratory properties.* J Leukoc Biol, 2011. 89(2): p. 311-7] some of the cells quantified as GR-MDSC in this study might have been granulocytes. Density gradient centrifugation of single milk samples, however, showed that all CD66b$^+$ cells sedimented with mononuclear cells at the interphase and did not pellet with polymorph nuclear cells, supporting our assumption that CD66$^+$ cells in BM are GR-MDSC. Much more important, however, is the fact that functional analyses of enriched milk CD66$^+$ cells revealed a high T-cell suppressive activity of these cells—the key distinguishing feature between GR-MDSC and granulocytes. Suppressive activity of BM-MDSC was even stronger than that of blood MDSC. Previous studies quantifying leukocyte subpopulations in BM found similar percentages of neutrophilic cells as the inventors did [Trend, S., et al., *Leukocyte Populations in Human Preterm and Term Breast Milk Identified by Multi-colour Flow Cytometry.* PLoS One, 2015. 10(8): p. e0135580., Maschmann, J., et al., *Characterization of human breast milk leukocytes and their potential role in cytomegalovirus transmission to newborns.* Neonatology, 2015. 107(3): p. 213-9]. Trend et al. analysed total milk cells and used a gating strategy to differentiate leukocyte subpopulations [Trend et al., loc. cit.] with CD16 as marker for mature neutrophils which can be also expressed by GR-MDSC [Brandau et al., loc. cit.; Kostlin et al., 2014, loc. cit.]. As they did not analyse the suppressive activity of these cells it remains unclear whether the cells they quantified were GR-MDSC or mature neutrophils. Maschmann et al. analysed mononuclear cells after density gradient centrifugation and used CD66b as surface marker making it likely that the cells they named neutrophils were in fact GR-MDSC [Maschmann et al., loc. cit.]. Based on our functional findings, we now suppose that most neutrophilic cells in BM are GR-MDSC.

Next, the inventors found that BM-MDSC exhibit an altered phenotype compared to blood GR-MDSC, with up-regulation of chemokine receptor CXCR4 and coinhibitory molecules PD-L1 and PD-L2. As discussed previously [Kostlin et al., 2016, loc. cit.], CXCR4 has been described as an MDSC activation marker in cancer [Obermajer, N., et al., *PGE(2)-induced CXCL12 production and CXCR4 expression controls the accumulation of human MDSCs in ovarian cancer environment.* Cancer Res, 2011. 71(24): p. 7463-70]. We have shown that CXCR4 was upregulated on placental MDSC and that blockade of CXCR4 reduced their suppressive activity [Kostlin et al., 2016, loc. cit.]. Similar to CXCR4, expression of PD-L1 on MDSC seems to be relevant for their suppressive activity [Lei, G. S., C. Zhang, and C. H. Lee, *Myeloid-derived suppressor cells impair alveolar macrophages through PD-1 receptor ligation during Pneumocystis pneumonia.* Infect Immun, 2015. 83(2): p. 572-82; Noman, M. Z., et al., *PD-L1 is a novel direct target of HIF-1alpha, and its blockade under hypoxia enhanced MDSC-mediated T cell activation.* J Exp Med, 2014. 211(5): p. 781-90], while to our knowledge PD-L2 expression on MDSC has not yet been described. Thus, upregulation of CXCR4, PD-L1 and PD-L2 on BM-MDSC points towards an activated state that is in line with our finding of an increased suppressive activity of these cells. Interestingly, it has been shown that high CXCL12 levels—the ligand for CXCR4—in breast milk were associated with reduced risk for HIV-transmission to breastfed infants [Farquhar, C., et al., *CC and CXC chemokines in breastmilk are associated with mother-to-child HIV-1 transmission.* Curr HIV Res, 2005. 3(4): p. 361-9]. The role of BM-MDSC and their regulatory functions for breastmilk-transmitted infections like HIV may be subject of further studies.

Concerning MDSC effector mechanisms the inventors found an increased expression of iNOS and a decreased production of ROS in BM-MDSC compared to GR-MDSC from peripheral blood of pregnant women, while expression of ArgI and IDO were not different. This expression pattern clearly differs from enzyme expression of GR-MDSC during pregnancy, where we found an upregulation of ROS production by placental GR-MDSC [Kostlin et al., 2016, loc. cit.]. Production of NO by iNOS was shown to decrease expression of MHCII molecules on macrophages and thereby inhibit T-cell activation [Kielar, M. L., et al., *Nitric oxide inhibits INFgamma-induced increases in CIITA mRNA abundance and activation of CIITA dependent genes—class II MHC, Ii and H-2M. Class II TransActivator.* Inflammation, 2000. 24(5): p. 431-45]. NO-production by cord blood MDSC led to induction of Tregs [Kostlin et al., 2017, loc. cit.]. Both mechanisms may play a role in regulating intestinal inflammation through BM-MDSC. The functional role of increased iNOS expression by BM-MDSC will be further evaluated. On the whole, BM-MDSC express a distinct pattern of surface- and effector-molecules reflecting BM as an immunological niche with specialized immune effector cells.

Furthermore, the inventors showed that BM-MDSC inhibit TLR4-expression on monocytes. TLR4 has been shown to play a critical role in NEC pathogenesis. TLR4-expression in intestinal mucosa was increased during NEC and lack of TLR4 in mice protected against NEC [Leaphart, C. L., et al., *A critical role for TLR4 in the pathogenesis of necrotizing enterocolitis by modulating intestinal injury and repair.* J Immunol, 2007. 179(7): p. 4808-20]. Interestingly, the NEC-protective effect of BM has been attributed to reduced TLR4 expression in intestinal epithelium [Good, M., et al., *Breast milk protects against the development of necrotizing enterocolitis through inhibition of Toll-like receptor 4 in the intestinal epithelium via activation of the epidermal growth factor receptor.* Mucosal Immunol, 2015. 8(5): p. 1166-79]. Given the inventors' present findings, it may be hypothesised that MDSC in breast milk protect against NEC by downregulating TLR4 on monocytes.

Moreover, the inventors aimed to identify factors responsible for the accumulation of MDSC in BM. Studies in mice revealed that the sex hormones estradiol and progesterone lead to an induction of MDSC during pregnancy and cancer [Pan, T., et al., *Myeloid-derived suppressor cells are essential for maintaining feto-maternal immunotolerance via STAT3 signaling in mice.* J Leukoc Biol, 2016; Pan, T., et al., *17beta-estradiol enhances the expansion and activation of myeloid-derived suppressor cells via STAT3 signaling in human pregnancy.* Clin Exp Immunol, 2016; Dong, G., et al., *17beta-estradiol contributes to the accumulation of myeloid-derived suppressor cells in blood by promoting TNF-alpha secretion.* Acta Biochim Biophys Sin (Shanghai), 2015. 47(8): p. 620-9.]. Immune-modulatory properties have also been described for the lactotrophic hormones prolactin and oxytocin [Costanza, M., et al., *Prolactin: a versatile regulator of inflammation and autoimmune pathology.* Autoimmun Rev, 2015. 14(3): p. 223-30; Iseri, S. O., et al., *Oxytocin protects against sepsis-induced multiple organ damage: role of neutrophils.* J Surg Res, 2005. 126(1): p. 73-81; Oliveira-Pelegrin, G. R., et al., *Oxytocin affects nitric oxide and cytokine production by sepsis-sensitized macrophages.* Neuroimmunomodulation, 2013. 20(2): p. 65-71]. However, the inventors found no effect of oxytocin or prolactin on MDSC induction. Thus, the mechanism of MDSC-accumulation in BM yet remains unclear. Other potential mediators for MDSC-accumulation in BM are the Th2 cytokines IL-4 and IL-13, for which an overexpression in the lactating mamma has been described [Watson, C. J., C. H. Oliver, and W. T. Khaled, *Cytokine signalling in mammary gland development.* J Reprod Immunol, 2011. 88(2): p. 124-9] and which are both implicated in the activation of MDSC [Highfill, S. L., et al., *Bone marrow myeloid-derived suppressor cells (MDSCs) inhibit graft-versus-host disease (GVHD) via an arginase-1-dependent mechanism that is up-regulated by interleukin-13.* Blood, 2010. 116(25): p. 5738-47; Gabitass, R. F., et al., *Elevated myeloid-derived suppressor cells in pancreatic, esophageal and gastric cancer are an independent prognostic factor and are associated with significant elevation of the Th2 cytokine interleukin-13.* Cancer Immunol Immunother, 2011. 60(10): p. 1419-30; Mandruzzato, S., et al., *IL4Ralpha+ myeloid-derived suppressor cell expansion in cancer patients.* J Immunol, 2009. 182(10): p. 6562-8]. Accordingly, the inventors found higher expression of IL4Rα in BM-MDSC than in GR-MDSC from peripheral blood of pregnant women; however, differences were not statistically significant. Examining the interactions between mammary epithelial cells and MDSC might give more insights in activation mechanisms of MDSC during lactation.

In conclusion, the inventors describe for the first time GR-MDSC in breast milk, showing an activated phenotype and modulating TLR-expression on monocytes. Their data suggest GR-MDSC and GR-MDSC exo as a promising target for modulating neonatal inflammatory response locally in the gut, potentially supporting establishment of the gut microbiome and potentially protecting neonates from NBI or NEC.

What is claimed is:

1. A method of preparing myeloid-derived suppressor cells (MDSC) comprising a step of isolating MDSC from breast milk, wherein the step of isolating MDSC from breast milk includes the following sub-steps:
   providing breast milk obtained from a breastfeeding female individual;
   centrifuging the breast milk to pelletize the milk cells;
   discarding the supernatant and washing the pelletized milk cells; and
   isolating the MDSC from the pelleted milk cells.

2. The method of claim 1, wherein the pelletized milk cells are incubated with an anti-MDSC antibody, followed by a separation of MDSC complexed with the anti-MDSC antibody, followed by a disengagement of the MDSC from the anti-MDSC antibody, thereby obtaining the MDSC.

3. The method of claim 2, wherein the anti-MDSC antibody is an anti-CD66b antibody.

4. The method of claim 1, wherein the MDSC comprise granulocytic myeloid-derived suppressor cells (GR-MDSC).

5. The method of claim 1, wherein the obtained MDSC are subjected to a density gradient centrifugation to separate granulocytic myeloid-derived suppressor cells (GR-MDSC) from monocytic myeloid-derived suppressor cells (MO-MDSC).

6. A method of preparing myeloid-derived suppressor cells (MDSC) derived exosomes (MDSC exo) comprising a step of isolating MDSC exo from breast milk.

7. The method of claim 6 comprising the following steps:
   providing isolated MDSC from breast milk,
   cultivating said isolated MDSC in cell culture medium,
   centrifuging said MDSC containing cell culture medium to obtain a supernatant and a pellet, and
   isolating MDSC exo from the supernatant.

8. The method of claim 7, wherein the isolation of MDSC exo from the supernatant includes one or more of the following procedures: centrifugation, ultracentrifugation, filtration, membrane filtration, microporous membrane filtration.

9. The method of claim 7, wherein the MDSC exo comprise granulocytic myeloid-derived suppressor cells derived exosomes (GR-MDSC exo).

10. A method of treatment of a living being, comprising the administration of myeloid-derived suppressor cells (MDSC) or MDSC derived exosomes (MDSC exo) isolated from breast milk.

11. The method of claim 10, wherein the MDSC comprise granulocytic myeloid-derived suppressor cells (GR-MDSC) and the MDSC exo comprise granulocytic myeloid-derived suppressor cells derived exosomes (GR-MDSC exo).

12. The method of claim 10, wherein said treatment is a treatment of a pathological condition selected from the group consisting of: bacterial infection, nosocomial bacterial infection (NBI), immune system disorder, inflammation, neonatal inflammation, enterocolitis, necrotizing enterocolitis (NEC), autoimmune disease.

13. The method of claim 12, wherein said living being is selected from the group consisting of: human new-born, human very low birth weight infant (VLBW).

* * * * *